US012594070B2

(12) United States Patent
Börner et al.

(10) Patent No.: US 12,594,070 B2
(45) Date of Patent: Apr. 7, 2026

(54) SUTURING DEVICE WITH IMPROVED NEEDLE TRANSFERRING MECHANISM

(71) Applicant: SUTURION AB, Ramlösa (SE)

(72) Inventors: Gabriel Börner, Ramlösa (SE); Hans Bengtsson, Eslöv (SE)

(73) Assignee: Suturion AB, Ramlösa (SE)

( * ) Notice: Subject to any disclaimer, the term of this patent is extended or adjusted under 35 U.S.C. 154(b) by 345 days.

(21) Appl. No.: 18/250,105

(22) PCT Filed: Oct. 25, 2021

(86) PCT No.: PCT/EP2021/079513
§ 371 (c)(1),
(2) Date: Apr. 21, 2023

(87) PCT Pub. No.: WO2022/084556
PCT Pub. Date: Apr. 28, 2022

(65) Prior Publication Data
US 2023/0389919 A1 Dec. 7, 2023

(30) Foreign Application Priority Data

Oct. 23, 2020 (EP) ..................................... 20203519

(51) Int. Cl.
*A61B 17/062* (2006.01)
*A61B 17/06* (2006.01)
(52) U.S. Cl.
CPC .... *A61B 17/0625* (2013.01); *A61B 17/06066* (2013.01); *A61B 2017/0609* (2013.01)

(58) Field of Classification Search
CPC .... A61B 2017/0609; A61B 2017/0469; A61B 2017/0625; A61B 2017/602;
(Continued)

(56) References Cited

U.S. PATENT DOCUMENTS 5,389,103 A 2/1995 Melzer et al.
5,571,090 A * 11/1996 Sherts ................ A61B 17/2909
606/139
(Continued)

FOREIGN PATENT DOCUMENTS

CA 3005638 A1 5/2017
EP 0705568 A1 4/1996
(Continued)

*Primary Examiner* — Katherine H Schwiker
(74) *Attorney, Agent, or Firm* — Dinsmore & Shohl LLP

(57) ABSTRACT

A one-handed automatic suturing device with a needle-transfer of a double-ended needle includes a first and a second jaw element that are movable in relation to each other between an open position and a closed position. The first jaw element has an alternating mechanism for alternating, each time the jaw elements are moved to the closed position, between: a retaining position, wherein the alternating mechanism is configured to retain a first end of the double-ended needle with a first retention strength; and a releasing position, wherein the alternating mechanism is configured for releasing said needle. The second jaw element has a holding mechanism for retaining and releasing a second end of the double-ended needle; wherein the holding mechanism is configured to retain the second end of the double-ended needle with a second retention strength that is lower than the first retention strength.

16 Claims, 9 Drawing Sheets

(58) Field of Classification Search
CPC .... A61B 2017/0491; A61B 2017/0482; A61B
2017/0483; A61B 2017/047; A61B
2017/0472; A61B 2017/0474; A61B
2017/0475; A61B 2017/0477; A61B
2017/0479; A61B 2017/048
See application file for complete search history.

(56) References Cited

U.S. PATENT DOCUMENTS

| | | |
|---|---|---|
| 2009/0177031 A1 | 7/2009 | Surti et al. |
| 2011/0022063 A1* | 1/2011 | McClurg ............ A61B 17/0469 606/147 |
| 2016/0066902 A1 | 3/2016 | Smith et al. |
| 2019/0059881 A1* | 2/2019 | Vrancken Peeters ........................ A61B 17/062 |

FOREIGN PATENT DOCUMENTS

| | | | |
|---|---|---|---|
| WO | 2008045353 A2 | 4/2008 | |
| WO | 2019/224269 A1 | 11/2019 | |
| WO | WO-2019224296 A1 * | 11/2019 | ......... A61B 17/0625 |
| WO | 2020006122 A1 | 1/2020 | |

* cited by examiner

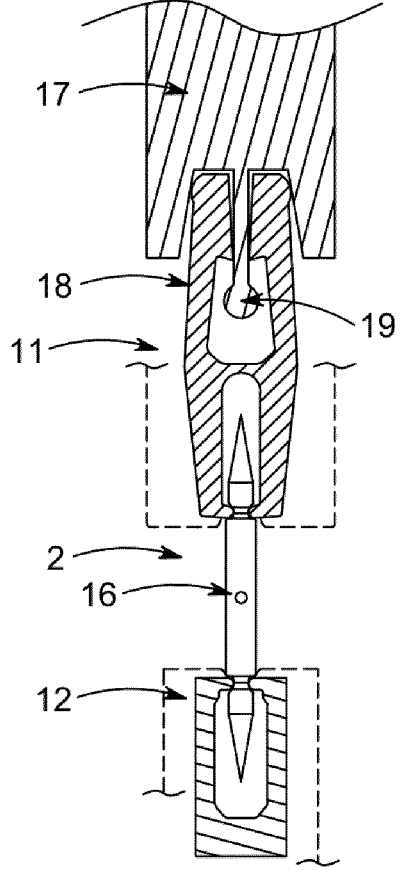
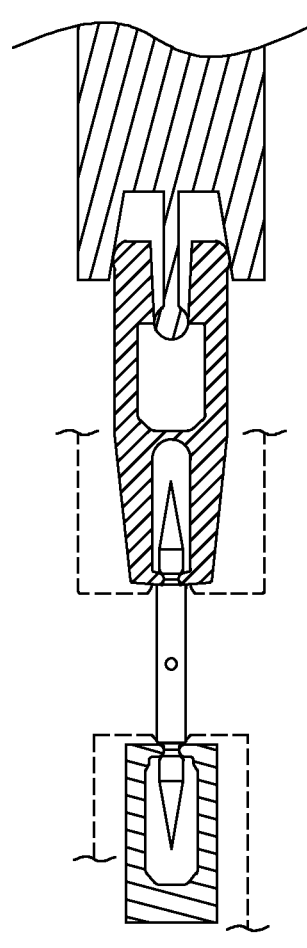
FIG. 2A                    FIG. 2B

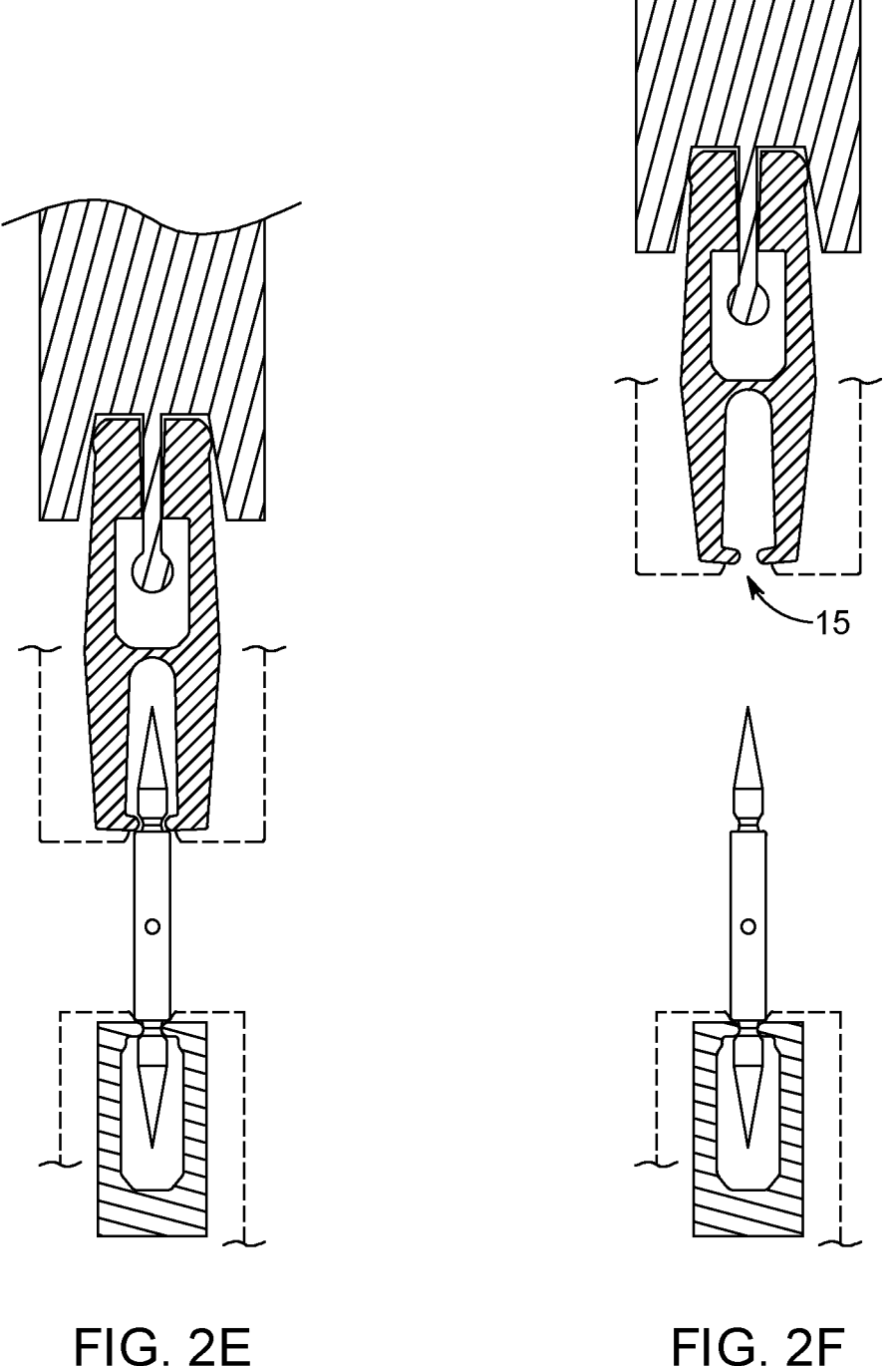
FIG. 2E                    FIG. 2F

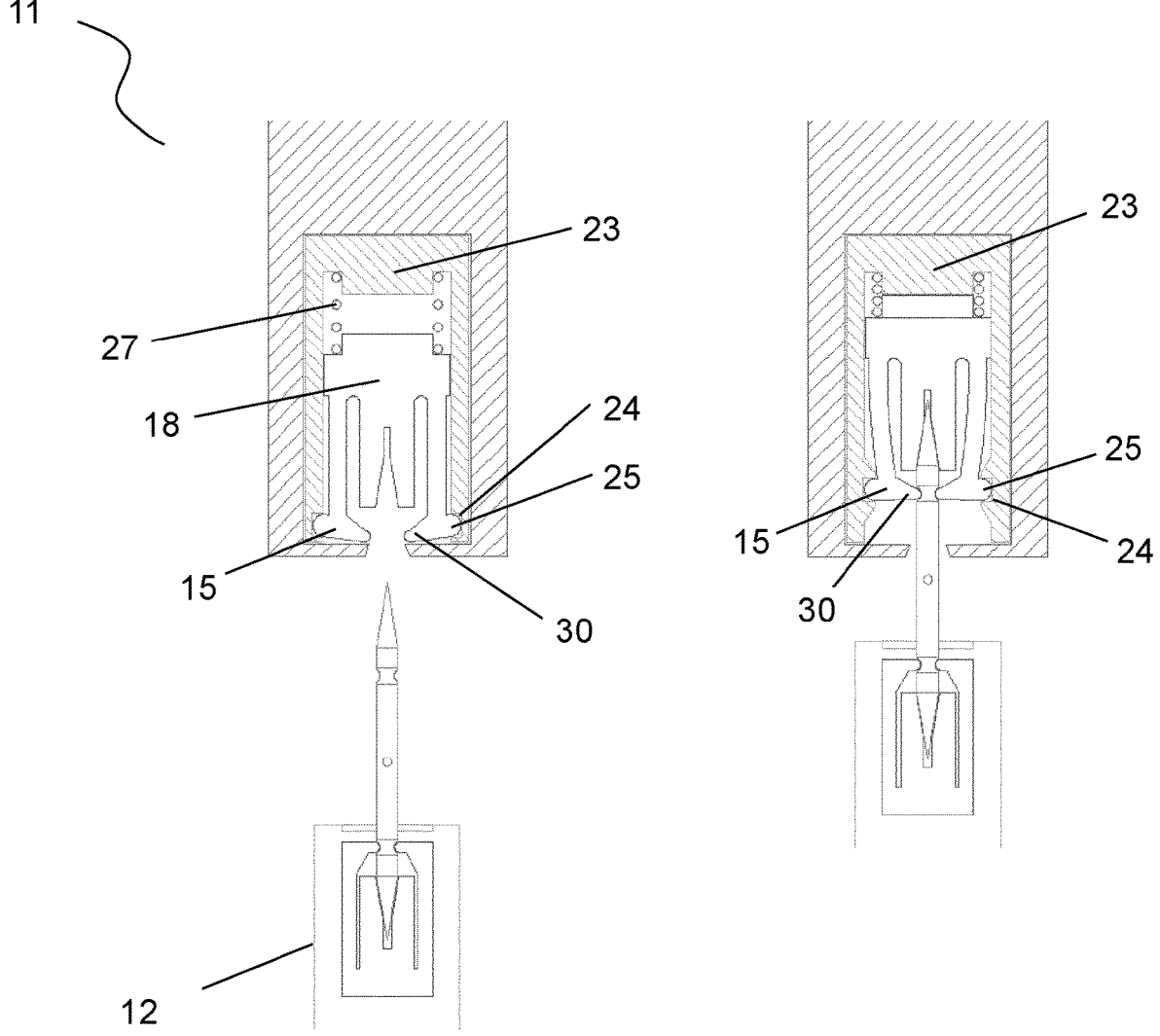
FIG. 4A                    FIG. 4B

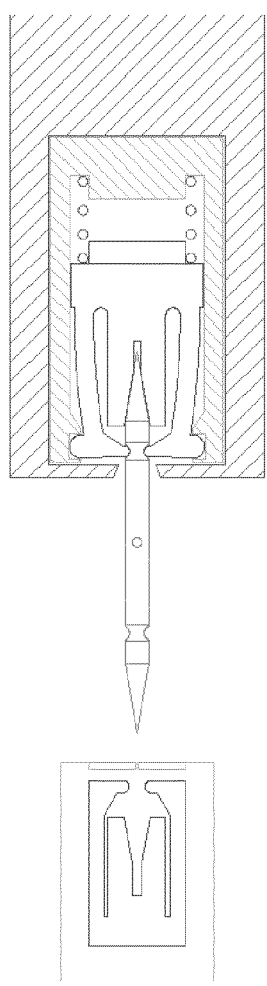
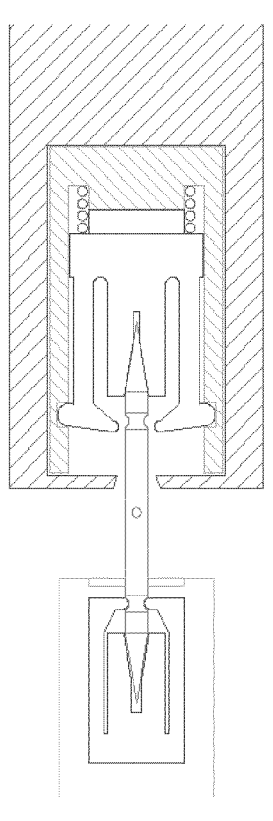
FIG. 4C                    FIG. 4D

SUTURING DEVICE WITH IMPROVED NEEDLE TRANSFERRING MECHANISM

CROSS-REFERENCE TO RELATED APPLICATIONS

This application is the U.S. National Stage of PCT/EP2021/079513 filed on Oct. 25, 2021, which claims priority to European Patent Application 20203519.2 filed on Oct. 23, 2020, the entire content of both are incorporated herein by reference in their entirety.

FIELD OF THE INVENTION

The present disclosure relates to an improved suturing device, in particular to an automated or semi-automated disposable suturing device. Preferably, the device is a one-handed suturing device.

BACKGROUND OF THE INVENTION

Surgical procedures in the abdominal cavity require access that can be achieved via open surgery or minimally invasive techniques. Open surgical procedures are very common and about 2 million procedures are performed annually in the US. The final step of the surgical intervention is the wound closure. Despite many advances in surgical techniques, equipment, and supplies, complications after abdominal wall closure remain a persistent problem. Ideally an abdominal closure should be efficient, provide strength, and serve as a barrier to infection. At the same time it should have low rates of fascial dehiscence, infection, hernia formation, suture sinus formation, and incisional pain. Experimental and clinical data gives sound information about the surgical technique required to minimize abdominal wall complications after surgery.

However, abdominal wound closure may be a tedious and time-consuming process, especially following a long and strenuous surgical procedure, potentially leading to an increased risk of complications. At the same time, closure of the abdomen is the most hazardous surgical moment for staff and surgeons due to the risk of prick injuries, posing a risk of transmission of infectious diseases. In addition, operating room time is expensive and time savings can provide care for more patients.

The existing suturing instruments are associated with a number of disadvantages and inconveniences. They are typically difficult to use, do not guarantee the safety of the patient, lack precision and are often mechanically complex. It would therefore be desirable to provide an instrument that would help the surgeon to adhere to the correct way of closing the abdomen and to reduce the time needed to perform the suturing. Preferably, such an instrument should also reduce the risk for prick injuries, simplify suture placement and be mechanically simple and robust while at the same time being light and compact for easy handling.

SUMMARY OF THE INVENTION

The present disclosure relates to an improved suturing device with built-in automatic needle-transfer of a double-ended needle. The suturing device may be a one-handed automatic suturing device, wherein the transfer of the needle between the jaws preferably is automatic in the sense that the mechanism for opening/closing of the jaws also controls, or is mechanically synchronized with, the transfer of the needle, preferably without the need of additional switches for controlling the transfer of the needle.

In a first embodiment the one-handed automatic suturing device comprises:

a first and a second jaw element that are movable in relation to each other between an open position and a closed position, wherein the first and second jaw elements are pivotable in relation to each other around a common pivot joint, and wherein:

a. the first jaw element comprises an alternating mechanism, wherein said alternating mechanism is configured to, upon the jaw elements being moved to the closed position by pushing the jaw elements together, automatically alternate between:

i. a retaining position, wherein the alternating mechanism is configured to retain a first end of the double-ended needle with a first retention strength; and ii. a releasing position, wherein the alternating mechanism is configured for releasing said needle;

b. the second jaw element comprises a holding mechanism for retaining and releasing a second end of the double-ended needle, wherein the holding mechanism is configured to retain a second end of the double-ended needle with a second retention strength that is lower than the first retention strength.

FIG. 1 shows an example of one-handed automatic suturing device comprising a double-ended needle, wherein the with the transfer of the needle back and forth between the first jaw element and the second jaw element is mechanically synchronized with the alternating mechanism. A user can hold the suturing device in one hand. When the jaw elements of the suturing device, which may have a general shape and operation similar to a handheld stapler, are pushed together, the alternating mechanism shifts from the retaining position to the releasing position, or from the releasing position to the retaining position. The alternating mechanism needs to be configured to handle both these transitions automatically when the jaw elements are pushed together. When the jaw elements are moved apart, the alternating mechanism stays in the position that it has taken after the jaw elements were pushed together. Preferably, the step of moving the jaw elements apart to an open position is done by a jaw opening spring or any other suitable element. For this there is typically an element, such a spring element or a flexible element, having inherent energy that can be used to move the jaw elements from a closed position to the open position. The user can then use a one-handed grip to push the jaw elements together and let the jaw elements flex back by releasing the grip. In this way transfer of the needle back and forth between the first jaw element and the second jaw element suturing can be done using one hand.

The presently disclosed suturing device with built-in needle-transfer provides an accurate and robust design of a suturing device for improved, in particular faster and more precise, surgical suturing, wherein a user may push the jaw elements together repeatedly using one hand to transfer the doubled-ended needle back and forth between the jaw elements. The process of transferring the needle from one jaw element to the other jaw element may be effectuated by a sequential mechanism inside the tool. In a preferred embodiment, the first jaw element comprises an alternating mechanism for alternating between a retaining position wherein the alternating mechanism is configured for retaining the double-ended needle, and a releasing position wherein the alternating mechanism is configured for releasing the double-ended needle. The alternating mechanism may be configured to alternate between said positions, for each time the suturing device is moved to the closed position from the open position. In a further preferred embodiment, the holding mechanism, located on the second jaw element, is a passive mechanism configured for retaining and releasing the double-ended needle.

It is a preference that the suturing device is configured such that the holding mechanism retains the second end of the double-ended needle when the alternating mechanism is in the releasing position and the first and a second jaw element are moved from the closed position to the open position, and the second end of the double-ended needle is released from the holding mechanism when the alternating mechanism is in the retaining position and the first and a second jaw element are moved from the closed position to the open position.

It is a further preference that the alternating mechanism is an active mechanism, that for example comprises parts that move in order to modify its function, and that the holding mechanism is a passive mechanism, that for example does not comprise parts that move in order to modify its function. The alternating mechanism may for example comprise parts that move, such as in response to a relative movement of the jaw elements, that modify its ability to retain the double-ended needle when the alternating mechanism is alternated between the retaining position and the releasing position, thereby modifying its retaining strength of the double-ended needle. It is a further preference that, contrary to the active mechanism of the alternating mechanism, the holding mechanism is a passive mechanism that does not comprise moving parts that modifies its ability to retain the double-ended needle. As such, the holding mechanism may be configured to retain the double-ended needle with a constant retaining strength.

It is a preference that the retention strength refers to the magnitude of a force, parallel to the axial length of the double-ended needle, that is required in order to pull a double-ended needle out from the holding mechanism or the alternating mechanism. While the holding mechanism is preferably a passive mechanism, associated with a constant retaining force, the alternating mechanism is an active mechanism preferably configured such that it alternates, upon closing of the jaw elements between the retaining position and the releasing position. In the releasing position, the alternating mechanism may be configured for retaining the double-ended needle with a third retaining strength that is a lower than the second retaining strength, or even a retaining strength that is substantially zero. Consequently, due to the first retaining strength being higher than the second retaining strength, that in turn is higher than the third retaining strength, alternating the alternating mechanism between being configured for retaining the double-ended needle with a high retaining strength and a low retaining strength, while the holding mechanism if constantly configured for retaining the double-ended needle with a retaining strength in between, the double-ended needle will be transferred between the jaw elements of the suturing device each time the sutured device is moved to the closed position and subsequently the open position.

BRIEF DESCRIPTION OF THE DRAWINGS

FIG. 4 shows a further exemplary alternating mechanism and holding mechanism.

DETAILED DESCRIPTION OF THE INVENTION

Figure 1A:
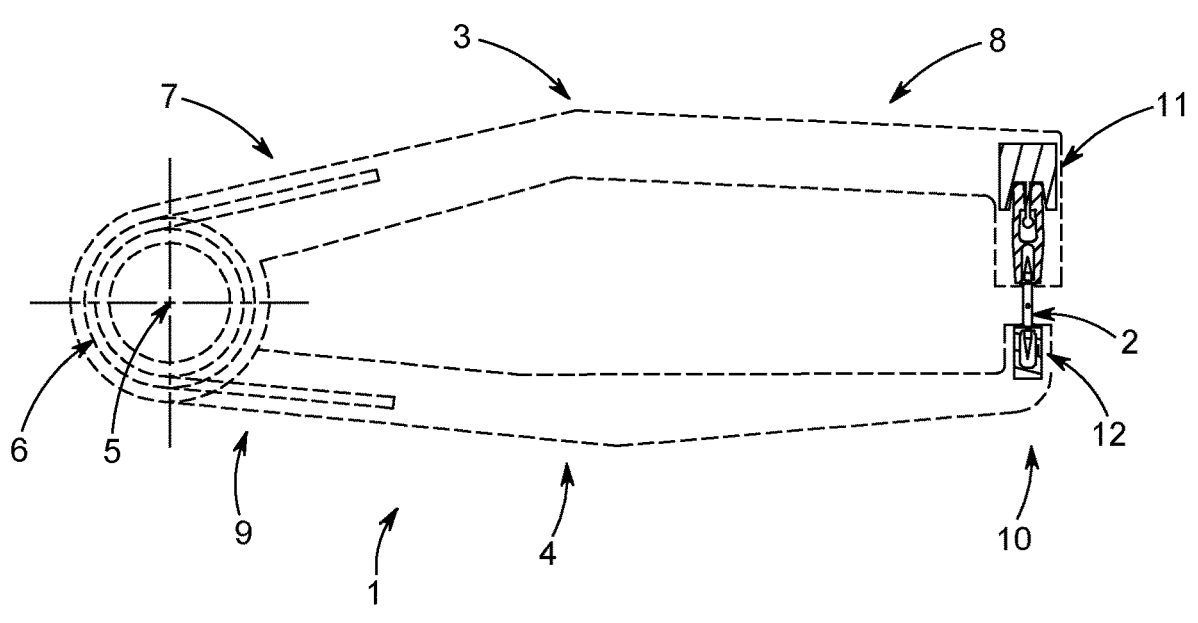
FIG. 1 shows a suturing device comprising a double-ended needle according to a specific embodiment of the present disclosure.

The present disclosure relates to a suturing device with a needle-transfer of a double-ended needle, the suturing device comprising a first and a second jaw element that are movable in relation to each other between an open position and a closed position. Preferably the user may hold the jaw elements in one hand and push the jaw elements together, thereby moving the suturing device from the open position to the closed position. It is a further preference that the first jaw element comprises an alternating mechanism for alternating, each time the jaw elements are moved to the closed position, between a retaining position and a releasing position. The retaining position is preferably configured to retain or hold a first end of the double-ended needle, such as with a first retention strength. The releasing position is preferably configured for releasing the double-ended needle. The second jaw element of the suturing device may comprise a holding mechanism that is configured for holding, and/or retaining and releasing, the double-ended needle, such as a second end of said double-ended needle. The holding mechanism may for example be configured to retain or hold the double-ended needle, such as the second end of said double-ended needle, with a second retention strength that is lower than the first retention strength. It is a further preference that the double-ended needle comprises a hole for a suture thread located between the first end and the second end of said double-ended needle.

In a specific embodiment of the present disclosure, the suturing device is configured such that the holding mechanism retains the second end of the double-ended needle when the alternating mechanism is in the releasing position and the first and a second jaw element are moved from the closed position to the open position, and the second end of the double-ended needle is released from the holding mechanism when the alternating mechanism is in the retaining position and the first and a second jaw element are moved from the closed position to the open position. In a further embodiment of the present disclosure, the alternating mechanism is configured such that it alternates between the releasing position and the retaining position once when the suturing device is moved from the open position to the closed position, or from the closed position to the open position. Thereby, the suturing device may be configured such that a complete cycle of the needle transfer mechanism is completed following moving of the suturing device to the closed position from the open position two times, and/or moving of the suturing device to the open position from the closed position two times. In an embodiment of the present disclosure, the alternating mechanism is an active mechanism and the holding mechanism is a passive mechanism. An active mechanism as used herein refers to a mechanism that comprises means for modification of its function, such as a modification of the ability to retain a double-ended needle. For example, an active mechanism may comprise parts that move in order to modify its function. The alternating mechanism is preferably an active mechanism that, for example, comprises a clamp unit and an activation unit, that when moved in relation to each other during the cycle of the needle transfer mechanism, such as when the alternating mechanism alternates from the releasing position to the retaining position, modifies the function of the alternating mechanism, i.e. the ability to retain the double-ended needle. Preferably, the alternating mechanism comprises a number of moving parts that upon movement of said parts, alternates the alternating mechanism from the retaining position to the releasing position. Contrary to this, a passive mechanism as used herein refers to a mechanism that does not comprise parts that move in order to modify its function. The holding mechanism for example is preferably a passive mechanism. As such, the retaining strength of the holding mechanism may be constant during the entire cycle of the needle transferring process of the suturing device. It should be noted that although the holding mechanism is a passive mechanism, it may comprise parts that are moved, displaced and/or deformed upon receiving the double-ended needle. For example, when the suturing device moves to the closed position, the double-ended needle may engage with the holding mechanism in a way that leads to movements, displacement and/or deformations of at least a part of the holding mechanism. However, this is typically not considered a modification of the function of the holding mechanism, but may instead be a part of the process, that is constant, of interaction or engaging, between the holding mechanism and the double-ended needle.

In an embodiment of the present disclosure, the suturing device is configured for transferring the double-ended needle between the first jaw element and the second jaw element, each time the jaw elements are moved to the closed position of the suturing device, such as from the open position of the suturing device. Typically, in the closed position, the double-ended needle directly contacts both the alternating mechanism and the holding mechanism. Thereby, transferring of the double-ended needle may refer to which of the two jaw elements or parts thereof, such as the alternating mechanism and the holding mechanism, that exerts the highest retaining strength on the double-ended needle. While both the alternating mechanism and the holding mechanism directly contacts the double-ended needle, one of said mechanisms may have a higher retaining strength on said needle. The mechanism, of the alternating mechanism and the holding mechanism that has a higher retaining strength on the double-ended needle, may be referred to as being in possession of the needle or that said mechanism retains the double-ended needle. Thereby, transferring of the double-ended needle may occur, or have occurred, even though both the alternating mechanism and the holding mechanism directly contacts the double-ended needle and/or while being directly contacted by the double-ended needle. In an embodiment of the present disclosure, the suturing device is configured such that the double-ended needle alternates between being contacted by the alternating mechanism and the holding mechanism, each time the jaw elements are moved to the open position, such as from the closed position.

Retention Strengths

In an embodiment of the present disclosure, the alternating mechanism, in the releasing position, is configured to retain the double-ended needle with a third retention strength that is lower than the second retention strength. In an embodiment of the present disclosure, the first retention strength is higher than the second retention strength, and the second retention strength is higher than the third retention strength. It is therefore a preference that the alternating mechanism alternates between holding on to the double-ended needle with a retention strength that is higher, when in retaining position, and lower, when in releasing position, than the retention strength of the holding mechanism. The holding mechanism preferably is configured to exert a retention strength that is constant during an entire cycle of the transferal of the double-ended needle of the suturing device. While obviously neither of the alternating mechanism and the holding mechanism makes continuous direct contact with the double-ended needle said mechanisms may be described herein as being configured for exerting a specific force on the double-ended, and/or having a specific retention strength, and/or being configure for holding the double-ended needle with a specific retention strength, these expression may be seen as identical and refer to the referred mechanism being configured for retaining the double-ended needle with the referred retention strength. Thereby, the alternating mechanism or the holding mechanism may have (i.e. be configured to hold the double-ended needle) with a specific retention strength, even though the double-ended needle is not present at said mechanism.

In an embodiment of the present disclosure, the third retention strength is substantially zero. Thereby, the magnitude of the third retention strength may be zero. For example, the alternating mechanism may be configured to not directly contact the double-ended needle in the releasing position, for example by opening of the clamp element. Thereby, the double-ended needle may be completely released, and if simultaneously engaged with the holding mechanism, the double-ended needle may be transferred to the holding mechanism during said movement to said releasing position.

In a further embodiment of the present disclosure, the first retention strength, the second retention strength and/or the third retention strength are defined as the forces required for displacing the double-ended needle from the alternating mechanism and the holding mechanism respectively, such as a magnitude of a force parallel to the axial length of the double-ended needle. The retention strength may be the force that is required in order to pull the double-ended needle out from the holding mechanism and the alternating mechanism.

In an embodiment of the present disclosure, the first retention strength is defined as the magnitude of a force, that is parallel to the axial length of the double-ended needle, that is required in order to pull said double-ended needle out from the alternating mechanism, such as in the retaining position of the alternating mechanism, such as away from the first jaw element. In an embodiment of the present disclosure, the second retention strength is defined as the magnitude of a force, that is parallel to the axial length of the double-ended needle, that is required in order to pull said double-ended needle out from the holding mechanism, such as away from the second jaw element. In an embodiment of the present disclosure, the third retention strength is defined as the magnitude of a force, that is parallel to the axial length of the double-ended needle, that is required in order to pull said double-ended needle out from the alternating mechanism, such as in the releasing position of the alternating mechanism, such as away from the first jaw element.

Double-Ended Needle/Surface Features

In an embodiment of the present disclosure, the double-ended needle comprises at least one surface feature, such as an indentation and/or a protrusion for engaging with the alternating mechanism and/or the holding mechanism. In another embodiment of the present disclosure, the double-ended needle comprises a first surface feature, such as an indentation and/or a protrusion for engaging with the alternating mechanism, and a second surface feature for engaging with the holding mechanism. In a specific embodiment of the present disclosure, the first end of the double-ended needle comprises a first surface feature and the second end of the double-ended needle comprises a second surface feature. The first end of the double-ended needle may be defined as the part of the double-ended needle facing or towards the alternating mechanism between the suture thread hole and the tip of the needle. The second end of the double-ended needle may be defined as the part of the double-ended needle towards or facing the holding mechanism between the suture thread hole and the tip of the needle.

In an embodiment of the present disclosure, each of the one or more surface features are located at different positions along the axial length of the double-ended needle, and extends around at least a part of the double-ended needle at said positions. The one or more surface features, such as a first surface feature, a second surface feature and any further surface features, are preferably located at different positions along the axial length of the double-ended needle. It is a further preference that the surface features extends, at least partly, around the double-ended needle, such as, at least partly, wraps around the double-ended needle. In an embodiment of the present disclosure, the one or more surface features have annular shapes, such as in a plane perpendicular to the axial length of the double-ended needle. In a preferred embodiment of the present disclosure, the needle has a circular cross-section, and the one or more surface is provided in the shape of an annulus, at a position along the axial length of the double-ended needle. For example a surface feature may be an indentation that wraps around at least a part of the double-ended needle, or a surface feature may be a protrusion that wraps around at least a part of the double-ended needle, typically at a position along the axial length of the double-ended needle. It is a preference that the first surface feature is located on the first end of the double-ended needle and that the second surface feature is located on the second end of the double-ended needle.

In an embodiment of the present disclosure, the alternating mechanism is configured to engage with the first surface feature, in the retaining position, for retaining the double-ended needle. The alternating mechanism is typically configured to directly contact the first surface feature, in the retaining position. In an embodiment of the present disclosure, the alternating mechanism is configured to engage with the first surface feature, in the releasing position, such as for releasing the double-ended needle. In an embodiment of the present disclosure, the alternating mechanism is configured to directly contact the first surface feature, in the releasing position. However, it is a preference that the alternating mechanism is configured for releasing the double-ended needle, in the releasing position. In an embodiment of the present disclosure, the alternating mechanism is configured for releasing the double-ended needle such that the double-ended needle is transferred to the holding mechanism, when said alternating mechanism is in the releasing position.

In yet an embodiment of the present disclosure, the holding mechanism is configured for engaging the second surface feature, for retaining the double-ended needle. In yet an embodiment of the present disclosure, the holding mechanism is configured for directly contacting the second surface feature, such as for retaining the double-ended needle. As disclosed elsewhere herein, the holding mechanism is preferably configured to retain the double-ended needle with a retaining strength that is lower than the retaining strength that the alternating mechanism is configured for retaining the double-ended needle within the retaining position of said alternating mechanism.

In a specific embodiment of the present disclosure, the first surface feature and/or the second surface feature has a rounding in a plane parallel with the to the axial length of the double-ended needle. The rounding may be constant around at least a part of the double-ended needle, at a specific location along the axial length of said double-ended needle. In a specific embodiment of the present disclosure, the configuration of the first surface feature, together with the configuration of the alternating mechanism, such as the clamp element, may result in the first retaining strength and the third retaining strength. Thereby, the configuration of the first surface feature, together with the configuration of the alternating mechanism, in the retaining position, may result in the first retaining strength. The configuration of the first surface feature, together with the configuration of the alternating mechanism, in the releasing position, may result in the third retaining strength. In a specific embodiment of the present disclosure, the configuration of the second surface feature, together with the configuration of the holding mechanism, such as the second complementary surface, may result in the second retaining strength.

Holding Mechanism

In an embodiment of the present disclosure, the holding mechanism comprises or consists of a snap-fit mechanism. A snap-fit is typically an assembly method used to attach parts, wherein at least one of said parts is flexible, typically a plastic, to form the final product by pushing the parts' interlocking components together. There are three main types of snap-fits: annular, cantilever, and torsional. Most snap-fit joints have a common design of a protruding edge and a snap-in area. The specific name of the snap-fit is usually named after the type of stress or strain it utilizes; the torsional snap-fit uses torque to hold parts in place.

The annular snap-fit utilizes hoop-strain to hold into place. Hoop-strain is the expansion of the circumference of the more elastic piece as it is pushed onto the more rigid piece. In most cases the design is circular. Some popular examples are pen caps, ball and socket joints, snap fasteners and some water bottle caps. This kind of snap-fit can be used multiple times. However, permanent strain may develop, loosening the joint when it is used too often. The cantilever snap-fit is the most commonly used snap-fit of the three. A cantilever design can be multiple use or permanent. A multiple use snap-fit usually has a lever or pin to be pushed, in order to undo the snap-fit. Similarly to Cantilever snap fits, in a torsional snap fit one must deflect, or force the protruding edges of piece B away from the insertion area. Piece A then slides in between the protruding edges until the desired distance is reached. The edges of piece B are then released and piece A is held in place. The snap-fits in this description are the protruding edges of piece B. These types of snap-fits may have a spring in place; so that when activated, the locked in piece is released and put into action.

In an embodiment of the present disclosure, the holding mechanism comprises a second complementary surface that is configured for engaging with at least a part of the second surface feature. In an embodiment of the present disclosure, at least one of the second surface feature and the second complementary surface comprises or consists of a protrusion and/or an indentation. In an embodiment of the present disclosure, both the second surface feature and the second complementary surface comprise or consist of a protrusion and/or an indentation. In a specific embodiment of the present disclosure, one of the second surface feature and the second complementary surface is a protrusion and the other is an indentation. In an embodiment of the present disclosure, the second complementary surface is configured to releasably engage or attach to the second surface feature, when the jaw elements are in the closed position. In a specific embodiment of the present disclosure, the second surface feature and the second complementary surface are configured for engaging according to a snap-fit mechanism. The second complementary surface may consequently be configured to comprise of consists of a protrusion that is configured to, upon receiving of the second end of the double-ended needle, by the holding mechanism, be deflected and engage the second surface feature. The holding mechanism may be configured to hold the double-ended needle, with a second retaining strength, when the second complementary surface has engaged with the second surface feature, such as deflected and mated with the second surface feature.

Alternating Mechanism

The alternating mechanism can be implemented in several ways. The alternating is, preferably linked to the action of closing the two jaw elements, which are pivotable in relation to each other around a common pivot joint. When the jaw elements are pushed together and the double-ended needle gets in contact with both jaw elements, this action, preferably, triggers a mechanical and automatic switch between the retaining position and the releasing position for the first jaw element. Since the holding mechanism is configured to retain the second end of the double-ended needle with a second retention strength that is lower than the first retention strength of the first jaw element, the double-ended needle is transferred back and forth between the two jaws by closing and opening the two jaws repeatedly.

In one embodiment the alternating mechanism is based on a clamp opening control element that is rotatable. Preferably, the clamp opening control element is rotatable around a vertical axis, i.e. an axis oriented in the same direction as the double-ended needle. An example of a such a clamp opening control element (23) is shown in FIG. 4A. The clamp opening control element (23) has, generally a substantially cylindrical shape. The clamp opening control element (23) may have a hollow interior in which a clamp unit (18) is disposed. The clamp opening control element (23) may have a cam guide (24) on the inside of the clamp opening control element (23). As the clamp opening control element (23) rotates, which happens when the clamp opening control element (23) moves upwards or downwards, a cam follower (25) of the clamp unit (18) changes circumferential position according to the shape of the cam guide (24).

An example is provided in FIGS. 4A-B. In FIG. 4A the clamp unit (18) is open. In FIG. 4B the jaw elements are pushed together. This has the effect that when the needle is received by the clamp unit (18) and pushes the same upwards, it causes the clamp opening control element (23) to rotate. In the new position the cam follower (25) is arranged in the cam guide (24) such that a hook element (30) holds the needle.

When the jaw elements are separated, as illustrated in FIG. 4C, the needle stays in the first jaw element, which can be said to be in the retaining position. The cam guide (24), which may have a generally, substantially, helical shape on the inside of the clamp opening control element (23) may be designed to include at least one blocking element in the form of, for example, a protrusion on the cam guide (24), such that the clamp unit (18) does not go back to the position of FIG. 4A.

In FIG. 4D the jaw elements are, again, pushed together. This has the effect that when the needle is received by the clamp unit (18) and pushes the same upwards, it causes the clamp opening control element (23) to rotate. In the new position, after the rotation, the cam follower (25) is arranged in the cam guide (24) such that a hook element (30) releases the needle.

The embodiment can be implemented applying adjustments and variations of the design to optimize the operation.

In a further embodiment, the alternating mechanism comprises a clamp element configured for engaging with, and/or directly contacting, the double-ended needle, in the retaining position of the alternating mechanism. The clamp element may be configured to engage, and/or directly contact, the first surface feature of the double-ended needle. The clamp element may comprise or consists of a first complementary surface that is configured for engaging with the first surface feature of the double-sided needle. In an embodiment of the present disclosure, the clamp element is configured to contact the first surface feature of the double-ended needle, in the retaining position of the alternating mechanism.

In an embodiment of the present disclosure, the alternating mechanism comprises an activation unit that is configured to translate substantially along the axial direction of the double-ended needle, and wherein the alternating mechanism is configured for alternating between the releasing position and the retaining position when said activation unit alternates between an upper position and a lower position.

In an embodiment of the present disclosure, the clamp element is provided at an end of a clamp unit, and wherein the activation unit is configured to engage the clamp unit in the retaining position and/or in the releasing position of the alternating mechanism. In an embodiment of the present disclosure, the clamp element is adapted such that said clamp element alternates between being configured for releasing and retaining the double-ended needed depending on the relative position of the clamp unit and the activation unit. In an embodiment of the present disclosure, the activation unit at least partly wraps around the clamp unit, or wherein the clamp unit at least partly wraps around the activation unit, in the retaining position and/or the releasing position.

In an embodiment of the present disclosure, the double-sided needle is automatically transferred between the first jaw element and the second jaw element upon closing and opening of the suturing device. In another embodiment of the present disclosure, the double-sided needle is automatically transferred between the first jaw element and the second jaw element upon opening and closing of the suturing device. It is a preference that the double-sided needle is transferred between the first jaw element and the second jaw element upon closing and opening of the suturing device.

In a specific embodiment of the present disclosure, the alternating mechanism comprises an activation unit and a clamp unit that are displaced with respect to each other, such as during a cycle of transferring the double-ended needle between the first and second jaw elements of the suturing device. The activation unit may comprise an activation mechanism that engages with the clamp unit. The clamp unit may comprise a clamp element that is configured to retain the double-ended needle, when the alternating mechanism is in the retaining position. In an embodiment of the present disclosure, the clamp element engages a first surface feature, located on a first end of the double-ended needle. Preferably, displacement of the activation unit with respect to the clamp unit, leads to an activation of the clamp unit. In an embodiment, of the present disclosure, the activation unit comprises an activation mechanism that engages with the clamp unit, and activates or deactivates the clamp element of the clamp unit, wherein activates refers to modifying the clamp element such that it is configured to retain the double-ended needle and deactivates refers to modifying the clamp element such that it is configured to release the double-ended needle. Preferably said activation and deactivation is a result of a displacement of the clamp unit with respect to the activation unit. Activation of the clamp element may result in the alternating mechanism being shifted to the retaining position while deactivation of the clamp element may result in the alternating mechanism to be shifted to the releasing position.

As mentioned, the movement of the activation unit with respect to the clamp unit may activate and/or deactivate the clamp unit. This may be achieved by providing, at least in parts, the alternating mechanism with an assembly similar, or identical, to a retractable pen. Specifically, the assembly of a retractable pen that extends and contracts the ballpoint out of the housing each time the pen is clicked as disclosed in U.S. Pat. No. 3,205,863. In a specific embodiment of the present disclosure, the alternating mechanism comprises a cam body, a plunger and a stop member. Preferably, the cam body is fixed to an upper end of the clamp unit or the activation unit. In another embodiment of the present disclosure, the cam body is connected, such as directly connected, to the activation unit and/or the clamp unit. Each time the suturing device is moved to the closed position, the alternating mechanism may be configured such that the activation unit is moved with respect to the clamp unit, for example the activation unit may alternate between an upper position and a lower position. The clamp unit may be configured such that deformation, separation and/or movement of a clamp element activator located at a first end of the clamp unit leads to activation and/or deactivation of the clamp element, for example similarly to a clothespin. The exemplified activation unit may comprise an activation surface that is configured to engage with a clamp element activators located at the first end of the clamp unit. The activation surface may be tapered, and the activation unit further comprises a wedge element located between the clamp activator units, such that movement of the activation unit with respect to the clamp unit either separates the clamp activator units or brings the clamp activator units together. Due to the configuration of the clamp unit, the distance between the clamp activator units may affect the state of the clamp element, located on the opposite side of the clamp unit. Separation of the clamp activator units, may lead to an activation of the clamp element, while bringing the clamp activator units together may lead to a deactivation of the clamp element. When the clamp element is activated, and engaged with the first surface feature of the double-ended needle, the alternating mechanism may be in the retaining position, and configured to retain a first end of the double-ended needle with a first retention strength. When the clamp element is deactivated, the alternating mechanism may be in the releasing position wherein the alternating mechanism is configured for releasing said needle Rotatable Wheel In another embodiment of the present disclosure, the suturing device comprises a rotatable wheel connected to the alternating mechanism. The rotatable wheel may be located at the pivot joint, or separate from the pivot joint. In an embodiment of the present disclosure the position of the alternating mechanism, e.g. releasing position and the retaining position, is not dependent on rotation of the rotatable wheel. In fact the rotatable wheel may disconnected, and/or not directly connected to the alternating mechanism. Instead the alternation of the alternating mechanism, wherein the alternating mechanism upon opening and/or closing of the suturing device alternates between the releasing position and the retaining position, may be a result of other mechanisms as disclosed elsewhere herein. It is a strong preference that the retaining strength of the holding mechanism is constant. Thereby, the retaining strength of the holding mechanism is not affected by for example the rotation of a rotatable wheel. The holding mechanism may not even be directly linked to such a rotatable wheel.

In an embodiment of the present disclosure, the suturing device therefore does not comprise a rotatable wheel. In another embodiment of the present disclosure, the suturing device comprises a rotatable wheel that is connected to the alternating mechanism, and the suturing device is configured such that opening and/or closing of the suturing device rotates the rotatable wheel. In such an instance, the rotatable wheel may be connected to the alternating mechanism and configured such that rotating of the rotatable wheel alternates the alternating mechanism between releasing position and retaining position.

In an embodiment of the present disclosure, a force is propagated from the first or second jaw element to the rotatable wheel, when the first and the second jaw elements are moved in relation to each other from the open position to the closed position, thereby causing the rotatable wheel to rotate. In a specific embodiment of the present disclosure, the rotatable wheel is arranged such that a rotation of the rotatable wheel causes the alternating mechanism to switch between the open position and the closed position.

Jaw Elements

In an embodiment of the present disclosure, a proximate end of the first jaw element is physically connected to a proximate end of the second jaw element. The jaw elements may together form a jaw. In an embodiment of the present disclosure, the alternating mechanism and the holding mechanism are located at distal ends of the jaw elements. Preferably, the alternating mechanism is located at a distal end of the first jaw element and the holding mechanism located at a distal end of the second jaw element. In a specific embodiment of the present disclosure, the jaw elements are pivotable in relation to each other around a common pivot joint. In an embodiment of the present disclosure, a rotatable wheel is located at the pivot joint. In a further embodiment of the present disclosure, the suturing device comprises a jaw opening spring arranged between the first jaw element and the second jaw element.

Opening Control Element

In one embodiment the presently disclosed suturing device comprises a jaw opening control element, which allows the user to manually control the rotatable wheels. There may also be two jaw opening control elements, one for each rotatable wheel, in order to be able to control the wheels individually. The jaw opening control element may be implemented, for example, as an extension of the rotatable wheels. The rotatable wheels may thereby have a first mechanical portion that is typically not directly exposed to the user. This portion may comprise the inner and outer portions of the rotatable wheel. These mechanical parts are typically placed behind a casing of the suturing device. The jaw opening control element may be an exposed part of the rotatable wheel, preferably comprising a grip or handle. The user can then control the locking and releasing of the needle manually by applying a force to the jaw opening control element. In an embodiment of the present disclosure, the suturing device comprises a clamp opening control element for manually controlling the position of the alternating mechanism, such as the retaining position and the releasing position. In another embodiment of the present disclosure, the suturing device is configured such that actuation of the clamp opening control element moves the alternating mechanism to the releasing position.

In an embodiment of the present disclosure, the needle-transferring mechanism is automatic or semi-automatic, preferably allowing for one-handed use. The transfer of the needle between the jaws may be automatic in the sense that the mechanism for opening/closing of the jaws also controls, or is mechanically synchronized with, the transfer of the needle, preferably without the need of additional switches for controlling the transfer of the needle. In a preferred embodiment of the present disclosure, the suturing device is disposable. This may be enabled, at least in part, by the fact that the device may be robust, efficient and relatively simple in its construction.

Detailed Description of Drawings

The invention will in the following be described in greater detail with reference to the accompanying drawings. The drawings are exemplary and are intended to illustrate some of the features of the presently disclosed suturing device, and are not to be construed as limiting to the presently disclosed invention.

Figure 1B:
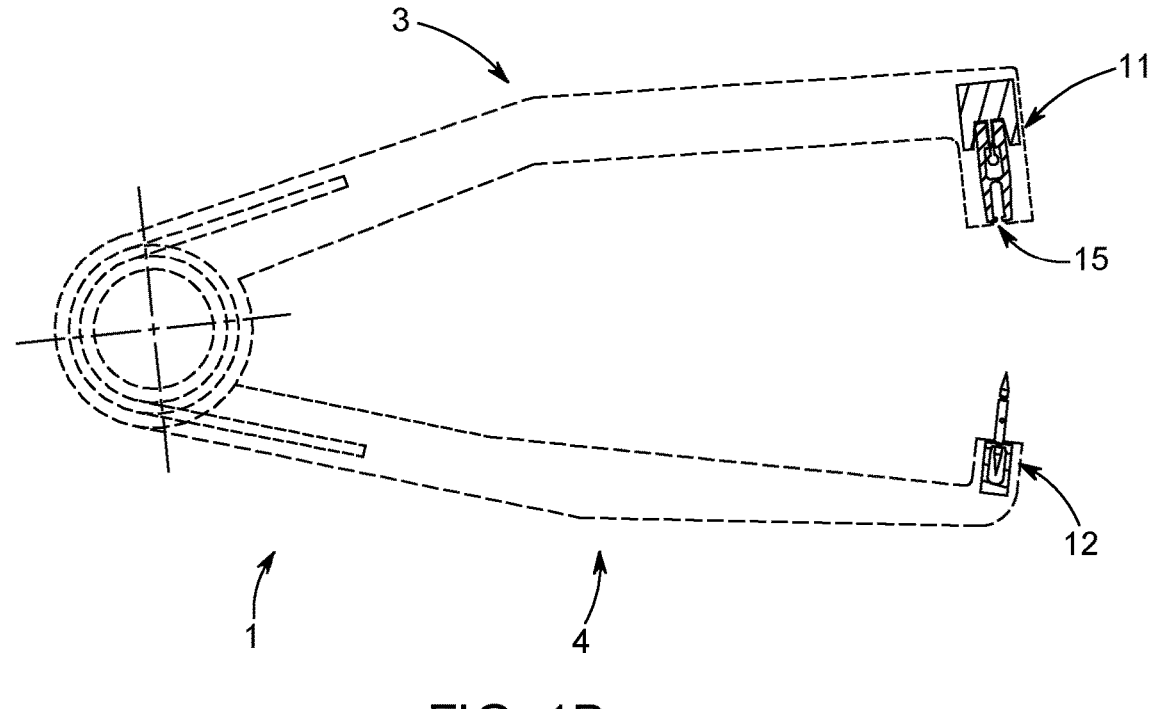

FIG. 1 shows one embodiment of the presently disclosed suturing device (1) with built-in needle-transfer of a double-ended needle (2), wherein said needle is transferred from a first jaw element (3) to a second jaw element (4) are pivotable in relation to each other around a common pivot joint (5). A jaw opening spring (6) is arranged between the proximate end of the first jaw element (7) and the proximate end of the second jaw element (9) that moves the jaws back to an open position after a user has pushed the jaw elements (3, 4) together to transfer the double-ended needle (2). The first jaw element (3) has an alternating mechanism (11), located at a distal end of the first jaw element. The second jaw element (4) has a holding mechanism (12) located at a distal end of the second jaw element (10). The suturing device in FIG. 1A is shown a closed position, wherein the distal ends of the jaw elements are close together. In this position the double-ended needle contacts both the alternating mechanism and the holding mechanism. The suturing device in FIG. 1B is shown an open position, wherein the distal ends of the jaw elements are far from each other. In this position the double-ended needle is in contact with only one of the alternating mechanism and the holding mechanism.

Figures 2C, 2D:
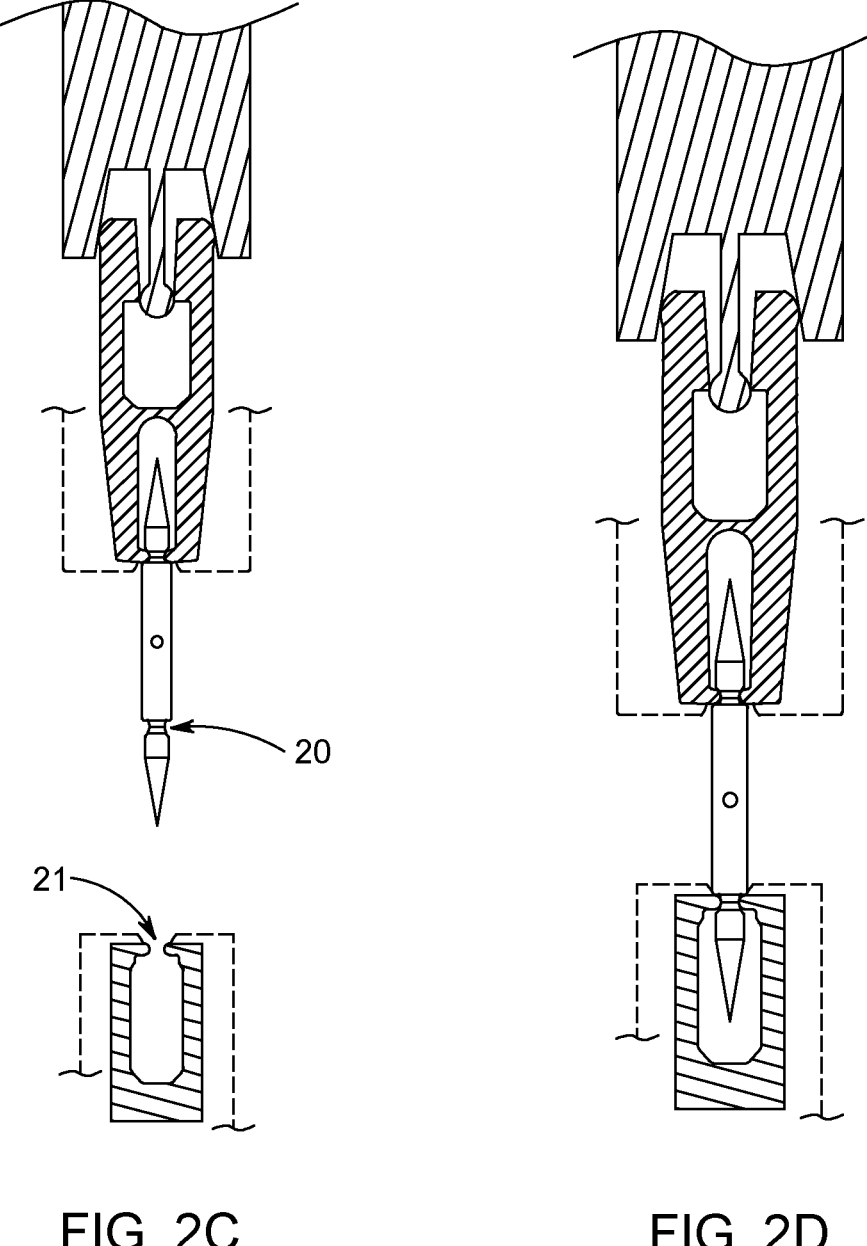
FIG. 2 shows an exemplary alternating mechanism and holding mechanism.

FIG. 2 shows an alternating mechanism and holding mechanism according to a specific embodiment of the present disclosure. In this embodiment, the holding mechanism (12) comprises a second complementary surface (21) that is configured for engaging with the double-ended needle. Specifically, the second complementary surface is configured for engaging with a second surface feature (20) located at a second end of the double-ended needle. The alternating mechanism (11), in this specific exemplary embodiment, comprises an activation unit (17) and a clamp unit (18) that are displaced with respect to each other. The activation unit comprises an activation mechanism that engages with the clamp unit (18). The clamp unit comprises a clamp element (15) that is configured to retain the double-ended needle, when the alternating mechanism is in the retaining position. The clamp element engages with a first surface feature (28), located on a first end of the double-ended needle (2). Displacement of the activation unit with respect to the clamp unit, leads to an activation of the clamp unit. The activation unit comprises an activation mechanism that engages with the clamp unit, and activates or deactivates the clamp element (15) of the clamp unit (18), when the clamp unit and the activation unit moves, with respect to each other. Activation of the clamp element should be understood as shifting of the alternating mechanism (11) to the retaining position, wherein the alternating mechanism is configured to retain the first end of the double-ended needle with a first retention strength. Deactivation of the clamp element should be understood as the shifting of the alternating mechanism (11) to the releasing position, wherein the alternating mechanism is configured for releasing the double-ended needle. In this example, the clamp element comprises two jaws, that, when the alternating mechanism (11) is in the retaining position, engages with the first surface feature (28) of the double-ended needle. When the alternating mechanism is in the releasing position, the two jaws of the clamp element opens up, and thereby releases the double-ended needle. The movement of the activation unit (17) with respect to the clamp unit (18) activates and deactivates said clamp unit. This may be achieved by providing, at least in parts, the alternating mechanism with an assembly similar, or identical, to a retractable pen. Specifically, the assembly of a retractable pen that extends and contracts the ballpoint out of the housing each time the pen is clicked, by a cam body, a plunger and a stop member, as disclosed in U.S. Pat. No. 3,205,863. The alternating mechanism of the present disclosure comprises a similar mechanism (not shown), wherein the cam body may be connected, such as directly connected, to the activation unit. Each time the suturing device is moved to the closed position, the activation mechanism alternates between an upper position and a lower position. The clamp unit may be configured such that deformation, separation and/or movement of the clamp element activator (29) located at a first end of the clamp unit (14) leads to activation and/or deactivation of the clamp element (15), much in a similar fashion as a clothespin. The exemplified activation unit comprises an activation surface (13) that engages with the clamp element activators (29) located at the first end of the clamp unit (14). The activation surface is tapered, and the activation unit further comprises a wedge element (19) located between the clamp activator units (29), such that movement of the activation unit (17) with respect to the clamp unit (18) wither separates the clamp activator units (29) or brings the clamp activator units (29) together. Due to the configuration of the clamp unit (18), the distance between the clamp activator units (29) affects the state of the clamp element, located on the opposite side of the clamp unit (18). Separation of the clamp activator units (29), leads to an activation of the clamp element (15), while bringing the clamp activator units (29) together leads to a deactivation of the clamp element (15). When the clamp element is activated, and engaged with the first surface feature (28) of the double-ended needle (2), the alternating mechanism (11) is in the retaining position, and configured to retain a first end of the double-ended needle with a first retention strength. When the clamp element is deactivated, the alternating mechanism (11) is in the releasing position wherein the alternating mechanism is configured for releasing said needle. In the releasing position, the alternating mechanism may either not be in contact with the double-ended needle, or the alternating mechanism may be in contact with the double-ended needle and configured for retaining said needle with a third retention strength, wherein the first retention strength is larger than the second retention strength that is larger than the third retention strength. Thereby, the second complementary surface (21) of the holding mechanism (12) may be configured, together with the second surface feature (20) of the double-ended needle, for retaining and releasing the second end of the double-ended needle with a second retention strength that is lower than the first retention strength. The holding mechanism, and the second surface feature, may for example be configured according to a snap-fit assembly, wherein the double-ended needle snaps in position when the second surface feature (20) of the double-ended needle engages with the second complementary surface (21) of the holding mechanism (12). FIG. 2A to FIG. 2F shows a cycle of transfer of the needle between the first jaw element and the second jaw element, starting from moving the suturing device to the closed position shown in FIG. 2A. This leads to the alternating mechanism (11) alternating from the releasing position, shown in FIG. 2A, to the retaining, shown in FIG. 2B. Here, the jaw elements have separated slightly, and during said separation the activation unit and moved, with respect to the clamp unit. This causes, as described above, activation of the clamp element (15) of the clamp unit (18), wherein the clamp element (15) engages the first surface feature (28), and retains the double-ended needle (2) with a first retention strength. As the first retention strength is higher than the strength by which the double-ended needle (2) is held by the holding mechanism (12), i.e. the second retention strength, upon opening the suturing device, FIG. 2C, the double-ended needle will be retained by the alternating mechanism. The suturing device is configured for one-handed use, such that the jaw elements are moved in relation to each other, between the open position and the closed position. Upon moving back to the closed state, FIG. 2D, the holding mechanism engages the double-ended needle, typically by engaging the second surface feature. This causes, such as together with further closing of the jaw elements, deactivation of the clamp element (15). By moving of the activation unit (17) with respect to the clamp unit (18), such that the wedge element disengages the first end of the clamp unit (14), while the activation surface (13) engages the activation unit (17). This causes the clamp element to be deactivated, and consequently, the alternating mechanism (11) to switch to the releasing position wherein the alternating mechanism is configured for releasing said needle, FIG. 2E. With the alternating mechanism in the releasing position, the clamp element may be separated from the double-ended needle, or the clamp element may be in contact with the double-ended needle, but holding on to said double-ended needle weakly, such as a third retention strength that is lower than the second retention strength. Thereby, when the suturing device is opened once again, the double-ended needle is retained by the holding mechanism, FIG. 2F. The process can thereafter be repeated such that the double-ended needle is transferred between the two jaw elements for each subsequent closing of the suturing device. Normally, the suture thread is connected to the double-ended needle through an aperture (16) at the center of the double-ended needle.

Figures 3A, 3B:
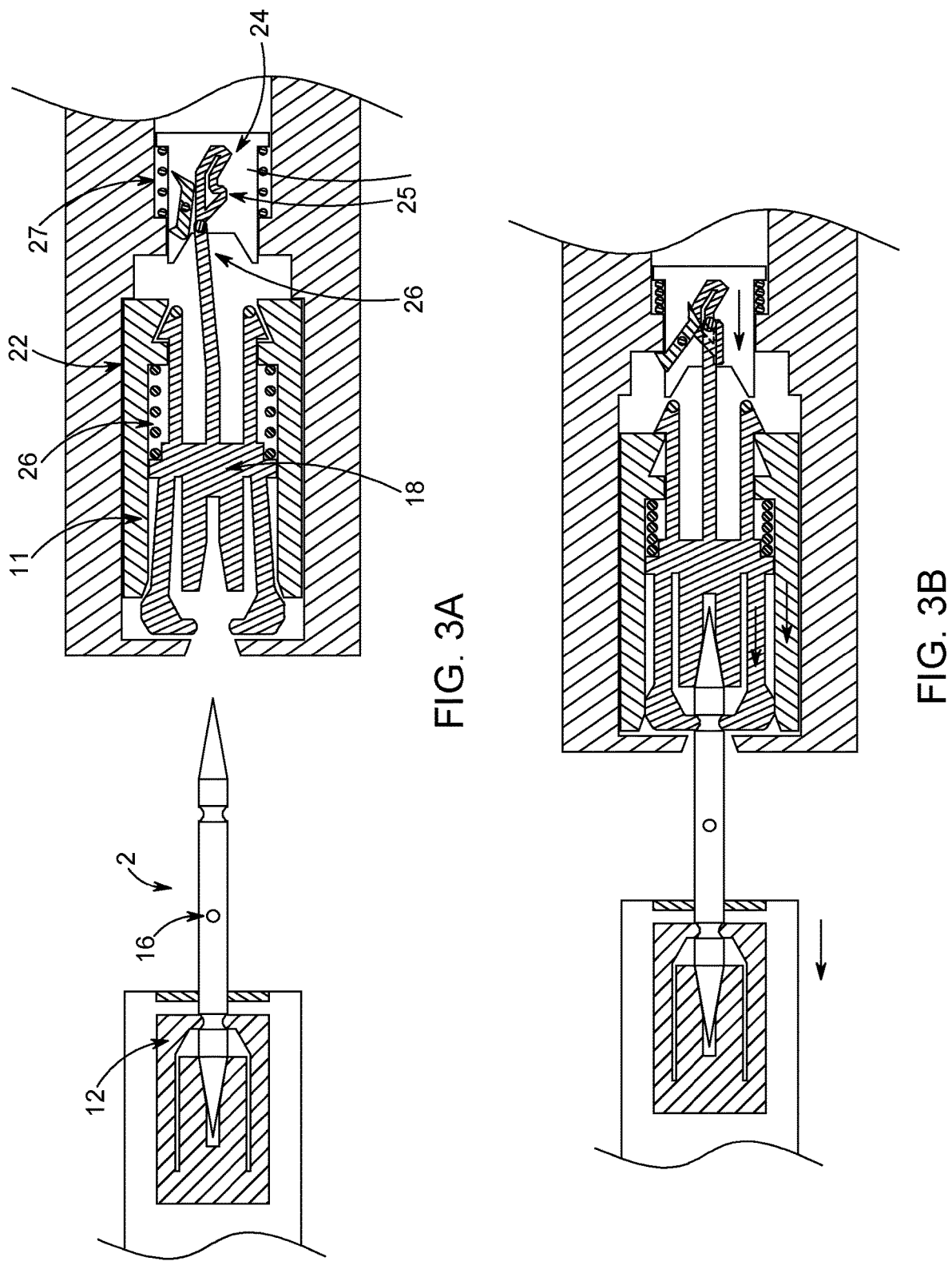
FIG. 3 shows an exemplary alternating mechanism and holding mechanism.
Figures 3C, 3D:
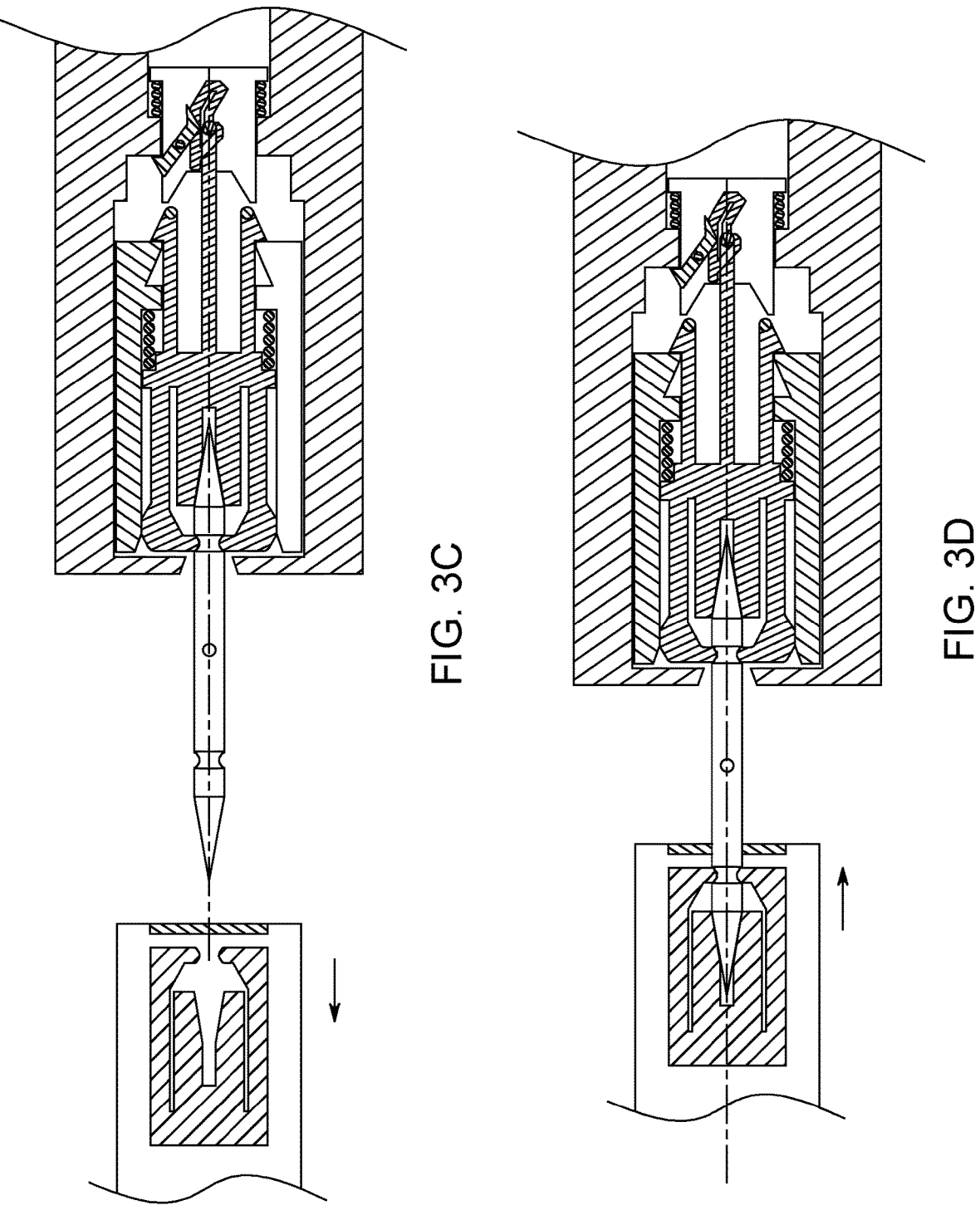
Figures 3E, 3F:
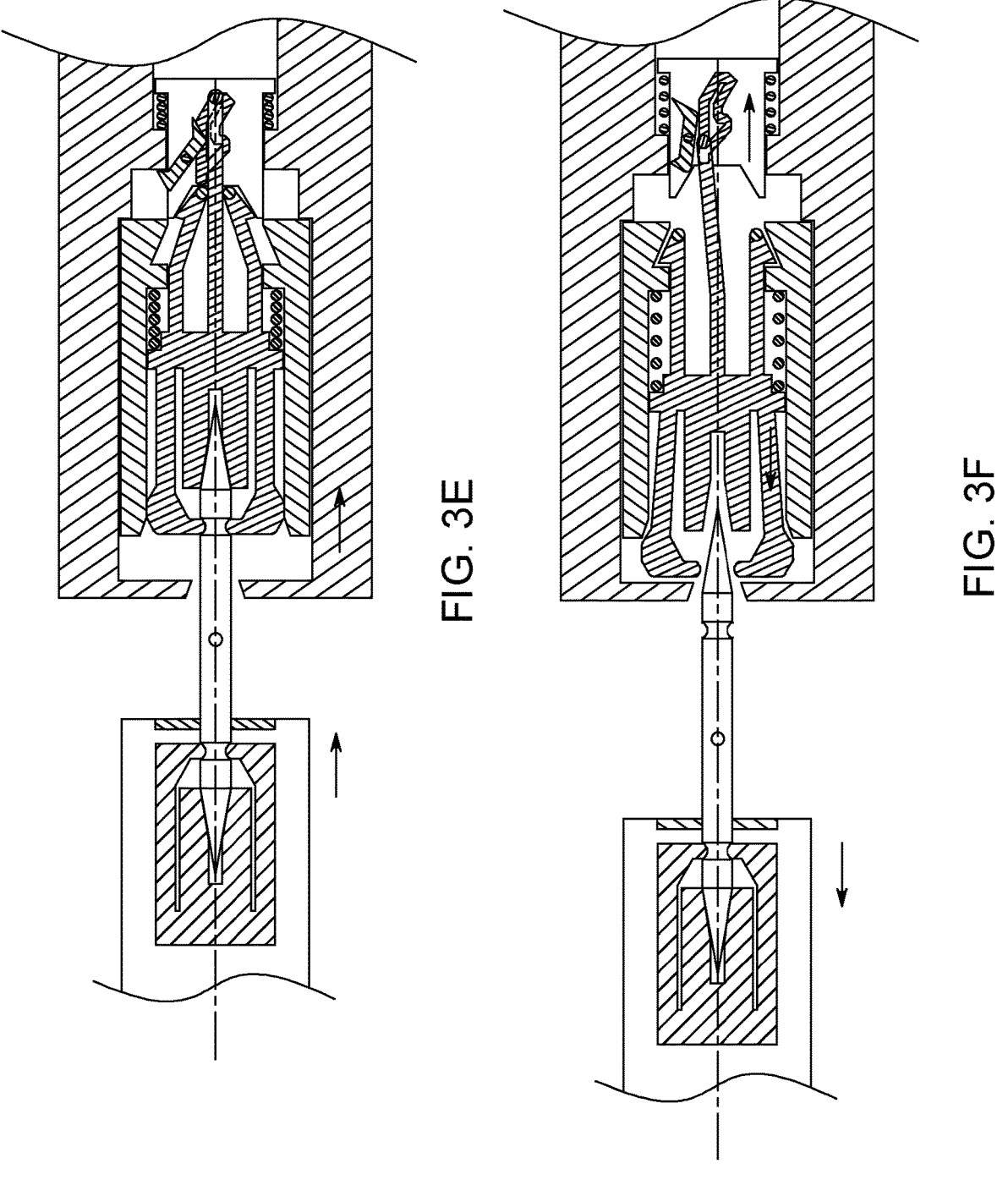

FIG. 3 shows an alternating mechanism and holding mechanism according to one embodiment of the present disclosure, configured for transferring a double-ended needle (2) between a first jaw element comprising an alternating mechanism (11) and a second jaw element comprising a holding mechanism (12). The alternating mechanism comprises an activation unit that is configured to alter the state of the clamp element by moving in relation to the clamp unit (18). The alternating mechanism (11) is switched to retaining position, upon moving of the activation unit (17) with respect to the clamp unit (18) such that the clamp element is configured for retaining the double-ended needle. Typically, this may be achieved by decreasing the distance between the clamp element (15) of the clamp unit (18) and/or by decreasing the ability for the clamp element to bend. The clamp unit is connected to a cam guide (24) of a clamp opening control element (23) through a cam follower (25). The cam follower (25), and thereby the clamp unit (18), follows a track of a cam guide (24) such that the clamp unit is moved with respect to the activation unit and/or the clamp opening control element (23). The alternating mechanism further comprises a first spring (26), for applying a force for axial separation of the clamp unit and the activation unit, and also a second spring (27) for axial separation of the clamp opening control element from the clamp unit and the activation unit. The clamp opening control element (23) further comprises a hook element (30) for maintaining the clamp opening control element (23) in a lower position, towards the clamp unit (18) and the activation unit (17). During a cycle of operation of the suturing device, the double-ended needle may initially be contacted by the holding unit (12), FIG. 3A. Following bringing of the two jaw elements together, the first end of the double-ended needle (2) engages with the alternating mechanism (11) and forces the clamp unit (18) upwards, towards the clamp opening control element (23). The clamp element (15) of the clamp unit thereby engage with the first surface feature (28) and apply a first retention strength on the double-ended needle (2), FIG. 3B. Upon opening of the jaw elements, the double-ended needle is retained by the alternating mechanism, as it holds on to said needle by a first retention strength that is larger than the second retention strength exerted on said needle by the holding mechanism (12), FIG. 3C. When again closing the jaw elements, FIG. 3D, the double-ended needle engages the holding mechanism, and again forces the clamp unit and the activation unit towards the clamp opening control element (23). A lower end of the clamp opening control element (23) is configured for engaging with an upper end of the clamp unit (18) having a tapered shape. This, together with the force of the first spring (26), leads to a movement of the clamp unit with respect to the activation unit, such that the clamp element (15) disengages the double-ended needle. The alternating mechanism is thereby in releasing mode. When the clamp unit moves to its lower position, the cam follower moves past the hook element (30) and interacts with it such that it is released, and the clamp opening control element (23) can return to its upper position. When opening the suturing device, the double-ended needle (2) is retained by the holding mechanism (12). This process may be repeated, and thereby each time the jaw elements move to the closed position from the open position, the double-ended needle is transferred between the jaw elements of the suturing device.

LIST OF ELEMENTS IN FIGURES 1. suturing device
2. double-ended needle
3. first jaw element
4. second jaw element
5. pivot joint
6. jaw opening spring
7. proximate end of first jaw element
8. distal end of first jaw element
9. proximate end of second jaw element
10. distal end of second jaw element
11. alternating mechanism
12. holding mechanism
14. first end of clamp unit
15. clamp element 16. hole for thread
17. activation unit
18. clamp unit
19. wedge element
20. second surface feature
21. second complementary surface
23. clamp opening control element
24. cam guide
25. cam follower
26. first spring
27. second spring
28. first surface feature
29. clamp element activator
30. hook element

Further Details of the Invention

1. A suturing device with a needle-transfer of a double-ended needle, the suturing device comprising:
   a first and a second jaw element that are movable in relation to each other between an open position and a closed position, and wherein:
   the first jaw element comprises an alternating mechanism for alternating, each time the jaw elements are moved to the closed position, between:
   a retaining position, wherein the alternating mechanism is configured to retain a first end of the double-ended needle with a first retention strength; and
   a releasing position, wherein the alternating mechanism is configured for releasing said needle;
   the second jaw element comprises a holding mechanism for retaining and releasing a second end of the double-ended needle, wherein the holding mechanism is configured to retain the second end of the double-ended needle with a second retention strength that is lower than the first retention strength.

2. The suturing device according to any one of the preceding items, wherein the suturing device is configured such that the holding mechanism retains the second end of the double-ended needle when the alternating mechanism is in the releasing position and the first and a second jaw element are moved from the closed position to the open position, and the second end of the double-ended needle is released from the holding mechanism when the alternating mechanism is in the retaining position and the first and a second jaw element are moved from the closed position to the open position.

3. The suturing device according to any one of the preceding items, wherein the alternating mechanism is an active mechanism and the holding mechanism is a passive mechanism.

4. The suturing device according to any one of the preceding items, wherein said suturing device is configured for transferring the double-ended needle between the first jaw element and the second jaw element, each time the jaw elements are moved to the closed position.

5. The suturing device according to any one of the preceding items, wherein said suturing device is configured such that the double-ended needle alternates between being contacted by the alternating mechanism and the holding mechanism, each time the jaw elements are moved to the open position.

6. The suturing device according to any one of the preceding items, wherein the alternating mechanism, in the releasing position, is configured to retain the double-ended needle with a third retention strength that is lower than the second retention strength.

7. The suturing device according to any one of the preceding items, wherein the first retention strength is higher than the second retention strength, and the second retention strength is higher than the third retention strength.

8. The suturing device according to any one of the preceding items, wherein the third retention strength is substantially zero, such as the magnitude of the third retention strength.

9. The suturing device according to any one of the preceding items, wherein the first retention strength, the second retention strength and/or the third retention strength are defined as the force required for displacing the double-ended needle from the alternating mechanism and the holding mechanism respectively, such as a magnitude of a force parallel to the axial length of the double-ended needle.

10. The suturing device according to any one of the preceding items, wherein the first retention strength is defined as the magnitude of a force, that is parallel to the axial length of the double-ended needle, that is required in order to pull said double-ended needle out from the alternating mechanism, such as in the retaining position of the alternating mechanism, such as away from the first jaw element.

11. The suturing device according to any one of the preceding items, wherein the second retention strength is defined as the magnitude of a force, that is parallel to the axial length of the double-ended needle, that is required in order to pull said double-ended needle out from the holding mechanism, such as away from the second jaw element.

12. The suturing device according to any one of the preceding items, wherein the third retention strength is defined as the magnitude of a force, that is parallel to the axial length of the double-ended needle, that is required in order to pull said double-ended needle out from the alternating mechanism, such as in the releasing position of the alternating mechanism, such as away from the first jaw element.

13. The suturing device according to any one of the preceding items, wherein the double-ended needle comprises at least one surface feature, such as an indentation and/or a protrusion.

14. The suturing device according to any one of the preceding items, wherein the first end of the double-ended needle comprises a first surface feature and/or the second end of the double-ended needle comprises a second surface feature.

15. The suturing device according to any one of the preceding items, wherein the one or more surface features are located at different positions along the axial length of the double-ended needle, and extends around at least a part of the double-ended needle at said positions.

16. The suturing device according to any one of the preceding items, wherein the one or more surface features have annular shapes, such as parallel to the axial length of the double-ended needle.

17. The suturing device according to any one of the preceding items, wherein the alternating mechanism is configured to contact the first surface feature, in the retaining position, for retaining the double-ended needle.

18. The suturing device according to any one of the preceding items, wherein the holding mechanism is configured for contacting the second surface feature, for retaining the double-ended needle.

19. The suturing device according to any one of the preceding items, wherein the first surface feature and/or the second surface feature has a rounding in a plane parallel with the to the axial length of the double-ended needle.

20. The suturing device according to any one of the preceding items, wherein the holding mechanism comprises or consists of a snap-fit mechanism.

21. The suturing device according to any one of the preceding items, wherein the holding mechanism comprises a second complementary surface that is configured for engaging with at least a part of the second surface feature.

22. The suturing device according to any one of the preceding items, wherein at least one of the second surface feature and the second complementary surface comprises or consists of a protrusion.

23. The suturing device according to any one of the preceding items, wherein both the second surface feature and the second complementary surface comprise or consist of a protrusion.

24. The suturing device according to any one of the preceding items, wherein one of the second surface feature and the second complementary surface is a protrusion and the other is an indentation.

25. The suturing device according to any one of the preceding items, wherein the second complementary surface is configured to releasably attach to the second surface feature, when the jaw elements are in the closed position.

26. The suturing device according to any one of the preceding items, wherein the alternating mechanism comprises a clamp element for contacting the double-ended needle, in the retaining position of the alternating mechanism.

27. The suturing device according to any one of the preceding items, wherein the clamp element is configured to contact the first surface feature of the double-ended needle, in the retaining position of the alternating mechanism.

28. The suturing device according to any one of the preceding items, wherein the alternating mechanism comprises a activation unit that is configured to translate substantially along the axial direction of the double-ended needle, and wherein the alternating mechanism is switched between the releasing position and the retaining position when said activation unit alternates between an upper position and a lower position.

29. The suturing device according to any one of the preceding items, wherein the clamp element is provided on an end of a clamp unit, and wherein the activation unit is configured to engage the clamp unit in the retaining position and/or in the releasing position.

30. The suturing device according to any one of the preceding items, wherein the activation unit at least partly wraps around the clamp unit, or wherein the clamp unit at least partly wraps around the activation unit, in the retaining position and/or the releasing position.

31. The suturing device according to any one of the preceding items, comprising a clamp opening control element rotatable around a vertical axis.

32. The suturing device according to item 31, wherein the clamp opening control element has a substantially cylindrical shape.

33. The suturing device according to any one of items 31-32, wherein comprises a cam guide, preferably on a hollow interior of the clamp opening control element.

34. The suturing device according to any one of items 31-33, wherein a corresponding cam follower of a clamp unit is arranged in the cam guide.

35. The suturing device according to any one of items 31-34, wherein the device is configured such that rotation of the clamp opening control element, caused by a vertical force on the clamp unit, causes the clamp opening control element to retain or release the double-ended needle.

36. The suturing device according to any one of the preceding items, wherein the alternating mechanism comprises a cam body and at least one stop member.

37. The suturing device according to any one of the preceding items, wherein the cam body is fixed to an upper end of the activation unit.

38. The suturing device according to any one of the preceding items, wherein the suturing device comprises a rotatable wheel connected to the alternating mechanism 39. The suturing device according to any one of the preceding items, wherein a force is propagated from the first or second jaw element to the rotatable wheel, when the first and the second jaw elements are moved in relation to each other from the open position to the closed position, thereby causing the rotatable wheel to rotate.

40. The suturing device according to any one of the preceding items, wherein the rotatable wheel is arranged such that a rotation of the rotatable wheel causes the alternating mechanism to switch between the open position and the closed position.

41. The suturing device according to any one of the preceding items, wherein a proximate end of the first jaw element is physically connected to a proximate end of the second jaw element, such that said jaw elements form a jaw.

42. The suturing device according to any one of the preceding items, wherein the alternating mechanism and the holding mechanism are located at a distal end of the jaw elements.

43. The suturing device according to any of the preceding items, wherein the jaw elements are pivotable in relation to each other around a common pivot joint.

44. The suturing device according to any one of the preceding items, wherein the rotatable wheel is located at the pivot joint.

45. The suturing device according to any of the preceding items, further comprising a jaw opening spring arranged between the first jaw element and the second jaw element.

46. The suturing device according to any of the preceding items, further comprising a clamp opening control element for manually controlling the position of the alternating mechanism.

47. The suturing device according to any of the preceding items, wherein actuation of the clamp opening control element moves the alternating mechanism to the open position.

48. The suturing device according to any of the preceding items, wherein the needle-transferring mechanism is automatic.

49. The suturing device according to any of the preceding items, wherein the suturing device is disposable.

The invention claimed is:

1. A one-handed automatic suturing device with automatic needle-transfer of a double-ended needle, the one-handed automatic suturing device comprising:

a first and a second jaw element that are movable in relation to each other between an open position and a closed position, wherein the first and second jaw elements are pivotable in relation to each other around a common pivot joint;

wherein;

the first jaw element comprises an alternating mechanism, wherein said alternating mechanism is an active mechanism configured to, upon the jaw elements being moved to the closed position by pushing the jaw elements together, automatically alternate between:

a retaining position, wherein the alternating mechanism is configured to retain a first end of the double-ended needle with a first retention strength; and a releasing position, wherein the alternating mechanism is configured for releasing said needle; and the second jaw element comprises a holding mechanism for retaining and releasing a second end of the double-ended needle, wherein the holding mechanism is configured to retain the second end of the double-ended needle with a second retention strength that is lower than the first retention strength;

wherein the holding mechanism is a passive mechanism configured to exert the second retention strength as a retention strength that is constant during an entire cycle of automatic needle-transfer of the double-ended needle; and wherein the second jaw element does not comprise an active mechanism configured to automatically alternate between a retaining position and a releasing position.

2. The one-handed automatic suturing device according to claim 1, further comprising a jaw opening spring arranged between the first jaw element and the second jaw element, wherein the jaw opening spring is configured to move the jaws back to the open position after a user has pushed the jaw elements together.

3. The one-handed automatic suturing device according to claim 1, wherein the transfer of the needle back and forth between the first jaw element and the second jaw element is mechanically synchronized with the alternating mechanism.

4. The one-handed automatic suturing device according to claim 1, wherein the one-handed automatic suturing device is configured such that the holding mechanism retains the second end of the double-ended needle when the alternating mechanism is in the releasing position and the first and the second jaw element are moved from the closed position to the open position, and the second end of the double-ended needle is released from the holding mechanism when the alternating mechanism is in the retaining position and the first and a second jaw element are moved from the closed position to the open position.

5. The one-handed automatic suturing device according to claim 1, wherein the alternating mechanism, in the releasing position, is configured to retain the double-ended needle with a third retention strength that is lower than the second retention strength.

6. The one-handed automatic suturing device according to claim 1, wherein the first retention strength is defined as the force required for displacing the double-ended needle from the alternating mechanism in the retaining position, the third retention strength is defined as the force required for displacing the double-ended needle from the alternating mechanism in the releasing position, and the second retention strength is defined as the force required for displacing the double-ended needle from the holding mechanism.

7. The one-handed automatic suturing device according to claim 1, wherein:

the first end of the double-ended needle comprises a first surface feature and the second end of the double-ended needle comprises a second surface feature; and the alternating mechanism is configured for engaging the first surface feature, in the retaining position, for retaining the double-ended needle, and wherein the holding mechanism is configured for engaging the second surface feature, for retaining the double-ended needle.

8. The one-handed automatic suturing device according to claim 7, wherein the alternating mechanism comprises a clamp element that is configured for engaging the first surface feature for retaining the double-ended needle, when the alternating mechanism is in the retaining position.

9. The one-handed automatic suturing device according to claim 7, wherein the holding mechanism comprises a second complementary surface that is configured for engaging with the second surface feature of the double-ended needle.

10. The one-handed automatic suturing device according to claim 9, wherein the holding mechanism and the second complementary surface are configured for engaging according to a snap-fit mechanism.

11. The one-handed automatic suturing device according to claim 9, wherein the one-handed automatic suturing device is configured such that the second complementary surface releasably attaches to the second surface feature, when the jaw elements are in the closed position.

12. The one-handed automatic suturing device according to claim 1, wherein the one-handed automatic suturing device comprises a rotatable wheel located at the pivot joint that is connected to the alternating mechanism, and configured such that, each time the first and the second jaw elements are moved in relation to each other from the open position to the closed position, the rotatable wheel rotates causing the alternating mechanism to switch between the open position and the closed position.

13. The one-handed automatic suturing device according to claim 1, further comprising a jaw opening spring arranged between the first jaw element and the second jaw element.

14. The one-handed automatic suturing device according to claim 1, further comprising a clamp opening control element for moving the alternating mechanism to the open position.

15. The one-handed automatic suturing device according to claim 1, wherein the double-sided needle is automatically transferred between the first jaw element and the second jaw element upon closing and opening of the one-handed automatic suturing device.

16. The one-handed automatic suturing device according to claim 1, wherein the one-handed automatic suturing device is disposable.

* * * * *